US00PP33531P2

(12) United States Plant Patent
Gomes da Costa

(10) Patent No.: US PP33,531 P2
(45) Date of Patent: Sep. 28, 2021

(54) ***ZAMIOCULCAS* PLANT NAMED 'TVZAMBL1'**

(50) Latin Name: *Zamioculcas zamiifolia*
Varietal Denomination: TVZAMBL1

(71) Applicant: Everton Gomes da Costa, Santo Antonio de Posse (BR)

(72) Inventor: Everton Gomes da Costa, Santo Antonio de Posse (BR)

(73) Assignee: Nicolaas Josef Schoenmaker e Outros, Sao Paulo (BR)

( * ) Notice: Subject to any disclaimer, the term of this patent is extended or adjusted under 35 U.S.C. 154(b) by 0 days.

(21) Appl. No.: 16/873,726

(22) Filed: Jun. 16, 2020

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP28,847 P3 * 1/2018 Spruit ..... A01H 5/12
Plt./373

OTHER PUBLICATIONS

UPOV-PLUTO: Plant Variety Database, Feb. 1, 2021, citation for 'TVZAMBL1'. (Year: 2016).*

* cited by examiner

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct *Zamioculcas* plant named 'TVZAMBL1', characterized by its compact and broadly upright plant habit; moderately vigorous to vigorous growth habit; and glossy leaflets that are close to pure black in color.

1 Drawing Sheet

Botanical designation: *Zamioculcas zamiifolia.*
Cultivar denomination: 'TVZAMBL1'.

STATEMENT REGARDING PRIOR DISCLOSURES BY INVENTOR/APPLICANT

An European Community Plant Breeder's Rights application for the instant plant was filed by the Assignee, Nicolaas Josef Schoenmaker e Outros of Sao Paulo, Brazil on Feb. 22 2016, application number 2016/0559. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct *Zamioculcas* plant, botanically known as *Zamioculcas zamiifolia*, and hereinafter referred to by the name 'TVZAMBL1'.

The new *Zamioculcas* plant is a naturally-occurring whole plant mutation of an unnamed selection of *Zamioculcas zamiifolia*, not patented. The new *Zamioculcas* plant was discovered and selected by the Inventor as a single plant from within a population of plants of the unnamed selection in a controlled environment in Sao Paulo, Brazil in May, 2012.

Asexual reproduction of the new *Zamioculcas* plant by vegetative cuttings in a controlled environment in Sao Paulo, Brazil since June, 2012, has shown that the unique features of this new *Zamioculcas* plant are stable and reproduced true to type in successive generations.

SUMMARY OF THE INVENTION

The cultivar TVZAMBL1 has not been observed under all possible combinations of environmental conditions and cultural practices. The phenotype may vary somewhat with variations in environment and cultural practices such as temperature and light intensity without, however, any variance in genotype.

The following traits have been repeatedly observed and are determined to be the unique characteristics of 'TVZAMBL1'. These characteristics in combination distinguish 'TVZAMBL1' as a new and distinct *Zamioculcas* plant:

1. Compact and broadly upright plant habit.
2. Moderately vigorous to vigorous growth habit.
3. Glossy leaflets that are close to pure black in color.

Plants of the new *Zamioculcas* can be compared to plants of the mutation parent selection. Plants of the new *Zamioculcas* differ primarily from plants of the mutation parent selection in leaf color as plants of the new *Zamioculcas* have close to pure black-colored leaves whereas plants of the mutation parent selection have medium green-colored leaves.

Plants of the new *Zamioculcas* can be compared to plants of *Zamioculcas zamiifolia* 'Dowon', disclosed in U.S. Plant Pat. No. 30,035. In side-by-side comparisons, plants of the new *Zamioculcas* differ from plants of 'Dowon' in the following characteristics:

1. Leaves of plants of the new *Zamioculcas* are darker in color than leaves of 'Dowon'.
2. Leaf petioles of plants of the new *Zamioculcas* are dark green in color whereas leaf petioles of plants of 'Dowon' are greyed green in color.

BRIEF DESCRIPTION OF THE PHOTOGRAPH

The accompanying colored photograph illustrates the overall appearance of the new *Zamioculcas* showing the colors as true as it is reasonably possible to obtain in colored reproductions of this type. Colors in the photograph may differ slightly from the color values cited in the detailed botanical description which accurately describe the colors of the new *Zamioculcas*.

The photograph (FIG. 1) is a side perspective view of a typical plant of 'TVZAMBL1' grown in a container.

DETAILED BOTANICAL DESCRIPTION

The aforementioned photographs and following observations, measurements and values describe plants of the new *Zamioculcas* grown during the winter and early spring in 15-cm containers in a glass-covered greenhouse in De Lier, The Netherlands and under cultural practices which closely approximate commercial production. During the production of the plants, day temperatures ranged from 21° C. to 30° C., night temperatures ranged from 18° C. to 20° C. and light levels averaged 12,000 lux. Plants were 18 months old when the photograph and the description were taken. In the detailed description, color references are made to The Royal Horticultural Society Colour Chart, 2015 Edition, except where general terms of ordinary dictionary significance are used.

Botanical classification: *Zamioculcas zamiifolia* 'TVZAMBL1'.

Parentage: Naturally-occurring whole plant mutation of an unnamed selection of *Zamioculcas zamiifolia*, not patented.

Propagation:

*Type.*—By vegetative cuttings.

*Time to initiate roots, summer.*—About 60 days at temperatures about 20° C. to 30° C.

*Time to initiate roots, winter.*—About 77 days at temperatures about 20° C. to 25° C.

*Time to produce a rooted young plant, summer.*—About 140 days at temperatures about 22° C. to 30° C.

*Time to produce a rooted young plant, winter.*—About 200 days at temperatures about 20° C. to 25° C.

*Root description.*—Medium in thickness to thick, fleshy; typically white to light brown in color, actual color of the roots is dependent on substrate composition, water quality, fertilizer type and formulation, substrate temperature and physiological age of roots.

*Rooting habit.*—Medium density; not freely branching.

*Tubers.*—Length: About 6.8 cm. Diameter: About 6.8 cm. Shape: Irregularly broadly oblong. Texture and luster: Smooth, glabrous; matte; cortical tissue, fleshy. Color, outer surface: Close to 199B to 199C. Color, cortical tissue: Close to 199D.

Plant description:

*Plant and growth habit.*—Compact and broadly upright plant habit; overall shape, inverted triangle; stemless; pinnately compound leaves developing in loose basal rosettes; typically about three basal rosettes develop per plant; suitable for 11-cm and larger containers; moderately vigorous to vigorous growth habit; moderate growth rate.

*Plant height.*—About 45 cm.

*Plant diameter.*—About 42.1 cm.

Leaf description:

*Arrangement.*—Pinnately compound; about twelve leaflets per leaf.

*Leaf length.*—About 38.4 cm.

*Leaf width.*—About 11.7 cm.

*Leaflet length.*—About 9.6 cm.

*Leaflet width.*—About 3.6 cm.

*Leaf shape.*—Oblong.

*Leaflet shape.*—Elliptic to oblong; slightly to moderately concave.

*Leaflet apex.*—Acute to short apiculate.

*Leaflet base.*—Attenuate.

*Leaflet margin.*—Entire to very slightly angulate.

*Leaflet texture, upper and lower surfaces.*—Smooth, glabrous.

*Leaflet texture, upper surface.*—Very glossy.

*Leaflet texture, lower surface.*—Glossy.

*Leaflet venation pattern.*—Pinnate.

*Color.*—Developing leaflets, upper surface: Darker than 147A and tinged with close to 202A. Developing leaflets, lower surface: Close to 146A. Fully expanded leaflets, upper surface: Close to 203A tinged with darker than 147A; venation, close to 203C tinged with darker than 147A. Fully expanded leaflets, lower surface: Slightly darker than 146A; venation, close to between 147A and 202A.

*Rachis.*—Length, base of leaf to lowest leaflet: About 21.2 cm. Diameter, at base of leaf: About 1 cm. Diameter, at lowest leaflet: About 4 mm. Strength: Moderately strong. Texture and luster: Smooth, glabrous; slightly glossy. Color, upper surface: Close to 197B slightly tinged with close to 148A. Color, lower surface: Close to 197B.

*Petiolule.*—Length: About 5 mm. Diameter: About 4 mm by 4.5 mm. Strength: Moderately strong. Texture and luster: Smooth, glabrous; slightly glossy. Color, upper surface: Close to 147A to 147B. Color, lower surface: Close to 147A.

*Geniculum.*—Length: About 11 cm. Diameter: About 9 mm to 21 mm. Strength: Moderately strong. Color, upper and lower surfaces: Close to 147A; distally, close to between 147A and 147B.

*Stipule.*—Length: About 7.8 cm. Diameter: About 2.6 cm. Shape: Ovate. Apex: Acute. Base: Broadly cuneate. Texture, upper and lower surfaces: Papery. Color, upper and lower surfaces: Close to 199D; towards the base, close to 200D; venation, close to 200B to 200C.

Flower description: To date, flower initiation and development has not been observed on plants of the new *Zamioculcas*.

Temperature tolerance: Plants of the new *Zamioculcas* have been observed to tolerate high temperatures about 40° C. and to suitable for USDA Hardiness Zones 10 to 12.

Pathogen & pest resistance: To date, plants of the new *Zamioculcas* have not been observed to be resistant to pathogens and pests common to *Zamioculcas* plants.

It is claimed:

1. A new and distinct *Zamioculcas* plant named 'TVZAMBL1' as illustrated and described.

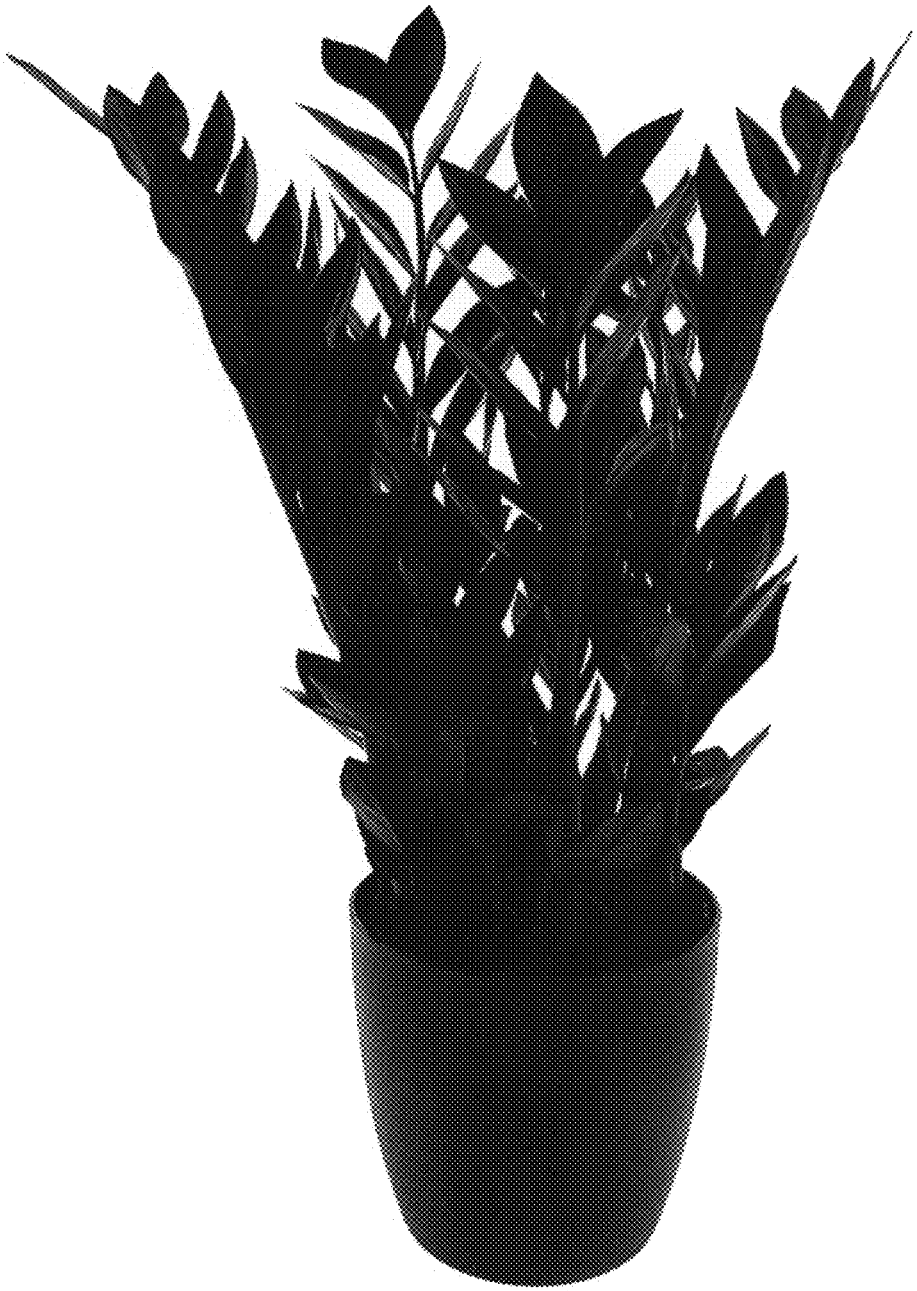

* * * * *